United States Patent [19]

Riitano et al.

[11] 3,961,422
[45] June 8, 1976

[54] STOP DEVICE FOR ENDODONTIC INSTRUMENTS

[76] Inventors: Francesco Riitano, Corso Umberto 1° (Palazzo Tiani), Soverato (Catanzaro); Vincenzo Spina, Via Fogliano,, 35 Rome, both of Italy

[22] Filed: Nov. 4, 1974

[21] Appl. No.: 520,953

[30] Foreign Application Priority Data
Nov. 8, 1973 Italy.................................... 4922/73

[52] U.S. Cl. .................................................. 32/57
[51] Int. Cl.² ............................................ A61C 5/02
[58] Field of Search............. 128/821, 367, DIG. 26; 32/59, 58

[56] References Cited
UNITED STATES PATENTS
3,330,040  7/1967  Kahn........................................ 32/57
3,388,473  6/1968  Loran..................................... 32/57

*Primary Examiner*—Robert Peshock
*Attorney, Agent, or Firm*—Robert E. Burns; Emmanuel J. Lobato; Bruce L. Adams

[57] ABSTRACT

A stop for limiting the depth of penetration of an elongated dental instrument usable in an endodontic operation. A diametrically bifurcated disc having a central instrument-receiving bore is comprised of two disc halves disposed in use with the elongated dental instrument extending through the central bore and clamped between the disc halves. A resilient snap-ring is seated in a circumferentially grooved lateral surface of the bifurcated disc to secure the two disc halves in position with the elongated dental instrument clamped therebetween.

4 Claims, 3 Drawing Figures

STOP DEVICE FOR ENDODONTIC INSTRUMENTS

BACKGROUND OF THE INVENTION

The present invention refers to the field of endodontia, that is, that sector of odontology referring to endodontotherapy, and relates in particular to the calibration of the working length of endodontic instruments used for the penetration, boring and drilling, widening and remodelling of dental radicular canals before their obturation.

The endodontic treatment is the preparation of the radicular canals for their whole length to allow the maximum removal of non-mineralized organic metter contained therein; the possibility of controlling the instruments during the dynamic working phase is based upon knowing first of all the length of the radicular canal so as to know how to preset the length of the working instrument.

DESCRIPTION OF THE PRIOR ART

At present, the length of the radicular canal is measured by means of X-ray radiography which permits the observation of a probe inserted into the canal and its reaching or not the apical border thereof.

After the useful penetration of the probe into the canal has been found and measured, the probe is withdrawn and used to fix "stops" to the shank of the instrument. According to different technical solutions these "stops" of the known art may be rubber rings, or locking rings and nuts.

The runner devices are light not very bulky, but present two drawbacks: one that they are easily subjected to sliding along the instrument; further that, having to be sterilized after the use of the endodontic instrument, the rubber soon loses its useful properties and deteriorates, being not resistant to high temperatures. The second drawback consists in the fact that, having to calibrate the same instrument more than once in the contact zone with the cutting edge which is supposed to slide with respect to the stop, the latter is exposed to cutting effects which endanger the duration and efficiency of the stop itself.

Other known stopping devices are, as already mentioned, formed of a group locking ring and nut easily stripped.

This group is clamped in the calibrated position on the endodontic instrument, the locking ring having a threaded, internally holed tang, grooved along proper generatrices angularly arranged one to the other so that they adhere under the required pressure to the surface of the instrument, when the ring nut is screwed onto the tang.

The following are the drawbacks of this type of stop:
a. A considerable bulk detrimental to the operation conditions which limits the use of the full length of the instrument;
b. To calibrate the instrument the locking ring nut has to be unscrewed to allow the movement between the instrument and the stop device; once the desired position has been obtained, the nut must be tightened to prevent any movement of the respective parts and considerable loss of time.

The known stop devices further to already described drawbacks are characterized by other ones caused for example by the fact that, the endodontic instrument being normally slightly tapered, the seal-on capacity of the stop has not always the same force values for the whole length of the instrument.

SUMMARY OF THE INVENTION

It is the main object of the present invention to obviate the above drawbacks and in particular to provide a stop device for endodontic instruments ensuring the perfect calibration at different positions and for endodontic instruments of different diameters, of small weight and bulk and made of materials which are sterilizing-agent-resistant.

Another object of the present invention is the realization of a device suitable for the quoted objects using a particularly simple structure of easy and safe operation.

These and other objects are achieved by the device of the present invention which, substantially, consists of a first component in the form of a half-disk with a groove along the circular lateral surface thereof and a semi-circular notch near the minor median axis of the front surface of the said half-disk normal to the plane of the said half-disk; a second component perfectly identical to the first one; a third component having the shape of an elastic interrupted ring of a section which perfectly adheres to the grooves of the two half-disks and securing them in such a manner as to keep them elastically clamped along the front surfaces.

BRIEF DESCRIPTION OF THE DRAWINGS

The properties and advantages of the present invention will be still better understood in view of the following description of a preferred embodiment of the present device but not limited thereto and the accompanying drawings, in which.

DESCRIPTION OF THE PREFERRED EMBODIMENT

Figure 1:
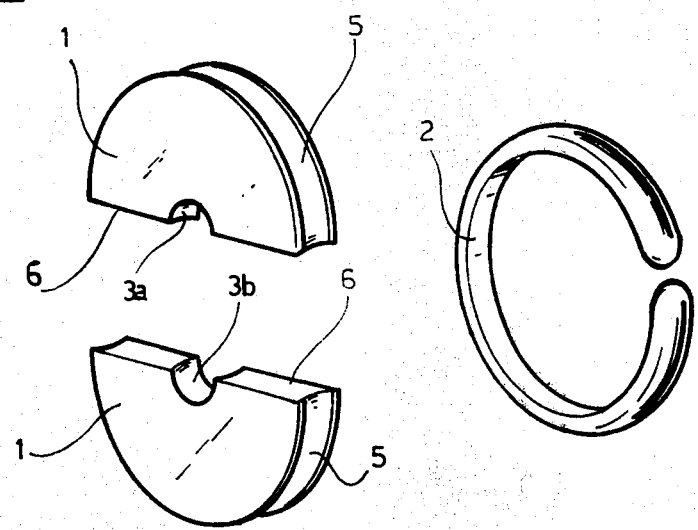
FIG. 1 is a blown-up view in perspective, considerably enlarged, of the components of the device composing the present invention.
Figure 2:
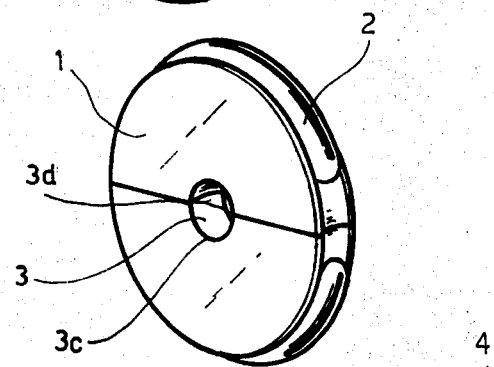
FIG. 2 is a perspective view of the whole device of the present invention.

With reference now to FIG. 1, it can be seen that the instrument stop according to the present invention, substantially consists of a diametrically bifurcated disc comprised of two half-disks 1 each one having along the circular rim thereof a groove 5 formed as a seat for an elastic, interrupted metal ring or resilient snap-ring 2 which, when seated in the said groove 5 elastically joins the half-disks 1 together so that the straight front rims 6 which are normal to the flat surface of the half-disks 1 are pressed one against the other.

Figure 3:
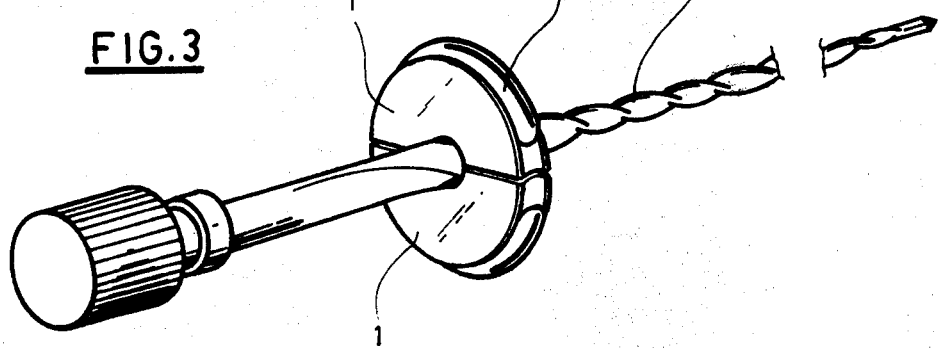
FIG. 3 is another perspective of the whole device showing, at a smaller scale than that of FIGS. 1 and 2, the stop mounted on an endodontic instrument.

The two half-disks 1 are provided each one with a semi-circular notch at the center of the straight rims, notches 3a and 3b which, when the half-disks are pressed together, form a hole or instrument-receiving bore 3 allowing the said stop device to be seated on an endodontic instrument, for example, as shown at 4 in FIG. 3.

When the two half-disks are closely joined along the straight edges 6 and kept together by the ring 2 seated within the circumferentially grooved lateral surface defined by grooves 5 of the disc halves 1, the diameter of the hole so formed is a minimum and receives the endodontic instrument at a well-defined distance of the stop from the vertex of the instrument.

To increase this distance it is sufficient to rotate the endodontic instrument around its axis with the stop firmly kept; the helical disposition of the instrument will allow in this case a deeper penetration thereof into and through the hole 3.

This increasing penetration expands the elastic ring 2 because of the taper of the instrument, forcing the straight edges 6 apart to lock the stop again in a position, in which the diameter of the instrument is larger than in the preceding position; the locking action is as before ensured by the pressure of the ring 2 on the half-disks 1.

The advantages of the present device as described hereinabove are evident from the disclosed embodiment.

Such a device as here described can be used for different instruments reducing in this way the number of similar devices to be made; it is still further advantageous because of its lightness and small bulk which are indispensable in the field of application it is intended for; in addition, all the parts thereof are made of metal or other idoneous materials which are supposed to be perfectly resistant to sterilizing agents.

According to a preferred form of embodiment, the hole 3 formed by the joining of the notches 3a and 3b is defined by a concave toroidal surface segment; this ensures that the friction between the endodontic instrument and the stop is limited to the edges 3c and 3d of the said hole 3 and reduces in this manner wear which, given the small diameters of the endodontic instruments (some hundredths of a millimeter), could reduce its life.

Obviously, the present invention is not limited to the embodiments here described and illustrated and that modifications and variations of construction can be applied thereto without leaving the scope of this invention and the accompanying claims.

What we claim and desire to secure by Letters Patent is:

1. The combination of an elongated dental instrument for use in an endodontic operation; and a stop for limiting the depth of penetration of the elongated dental instrument during the endodontic operation; said stop comprising: a diametrically bifurcated disc having a central instrument-receiving bore extending therethrough in a direction generally normal to the plane of the disc and dimensioned for snugly receiving the elongated dental instrument, and having a circumferentially grooved outer lateral surface, said bifurcated disc comprising two disc halves disposed in use about the elongated dental instrument with the elongated dental instrument extending through the instrument-receiving bore and clamped between the two disc halves, and positioned in use along the elongated dental instrument to limit the depth of penetration thereof; and a resilient snap-ring dimensioned to fit within the circumferentially grooved lateral surface and secure the two disc halves in position with the elongated dental instrument clamped therebetween.

2. The combination according to claim 1, wherein the central instrument-receiving bore is defined by a concave toroidal surface segment.

3. A stop, for limiting the depth of penetration of an elongated dental instrument usable in an endodontic operation, which comprises: a diametrically bifurcated disc having a central instrument-receiving bore extending therethrough in a direction generally normal to the plane of the disc, and having a circumferentially grooved outer lateral surface, said bifurcated disc comprising a pair of disc halves positionable in use to jointly define said bifurcated disc; and a resilient snap-ring dimensioned to fit within the circumferentially grooved lateral surface to secure the two disc halves together to define said bifurcated disc.

4. A stop according to claim 3, wherein the central instrument-receiving bore is defined by a concave toroidal surface segment.

* * * * *